United States Patent [19]
Ramsey, III et al.

[11] Patent Number: 5,170,795
[45] Date of Patent: Dec. 15, 1992

[54] OSCILLOMETRIC BLOOD PRESSURE MONITOR AND METHOD EMPLOYING NON-UNIFORM PRESSURE DECREMENTING STEPS

[75] Inventors: Maynard Ramsey, III, Tampa; Richard Medero, Lutz; Rush W. Hood, Jr., Tampa, all of Fla.

[73] Assignee: Critikon, Inc., Tampa, Fla.

[21] Appl. No.: 923,374

[22] Filed: Oct. 27, 1986

Related U.S. Application Data

[63] Continuation-in-part of Ser. No. 751,840, Jul. 5, 1985, abandoned, and a continuation-in-part of Ser. No. 751,827, Jul. 5, 1985, abandoned.

[51] Int. Cl.$^5$ .............................................. A61B 5/02
[52] U.S. Cl. .................................... 128/682; 128/680
[58] Field of Search ................................ 128/677–683

[56] References Cited

U.S. PATENT DOCUMENTS

| | | | |
|---|---|---|---|
| 4,009,709 | 3/1977 | Link et al. | 128/683 |
| 4,137,907 | 2/1979 | Jansen et al. | 128/681 |
| 4,271,843 | 6/1981 | Flynn | 128/681 |
| 4,313,445 | 2/1982 | Georgi | 128/682 |
| 4,461,266 | 7/1984 | Hood, Jr. et al. | 128/681 |
| 4,625,277 | 11/1986 | Pearce et al. | 128/680 |
| 4,638,810 | 1/1987 | Ramsey, III et al. | 128/681 |
| 4,669,485 | 6/1987 | Russell | 128/679 |

FOREIGN PATENT DOCUMENTS 1163327 3/1984 Canada .............................. 128/677

OTHER PUBLICATIONS

"The Norse Systems Automatic BP Monitor" by Link et al, Internal Memo of Norse Systems Inc Nov. 1974.

Primary Examiner—David Shay
Attorney, Agent, or Firm—Audley A. Ciamporcero, Jr.

[57] ABSTRACT

A blood pressure cuff is applied about a subject's artery, and inflated above the systolic level thus fully occluding the artery for a full heart cycle. The cuff pressure is thereafter reduced to permit an increasing flow through the progressively less occluded artery, and a measure of the peak amplitudes of the successively encountered blood pressure (oscillatory complex) pulses stored in memory. Also retained is the cuff pressure obtaining for each stored complex peak. In accordance with varying aspects of the present invention, the stored complex peak-representing data ensemble is corrected for aberrations; and improved data processing operates on the stored (and advantageously corrected) pulse peak data and the corresponding cuff pressure information to determine the subject's systolic arterial blood pressure.

7 Claims, 10 Drawing Sheets

DATA PURIFICATION ROUTINE

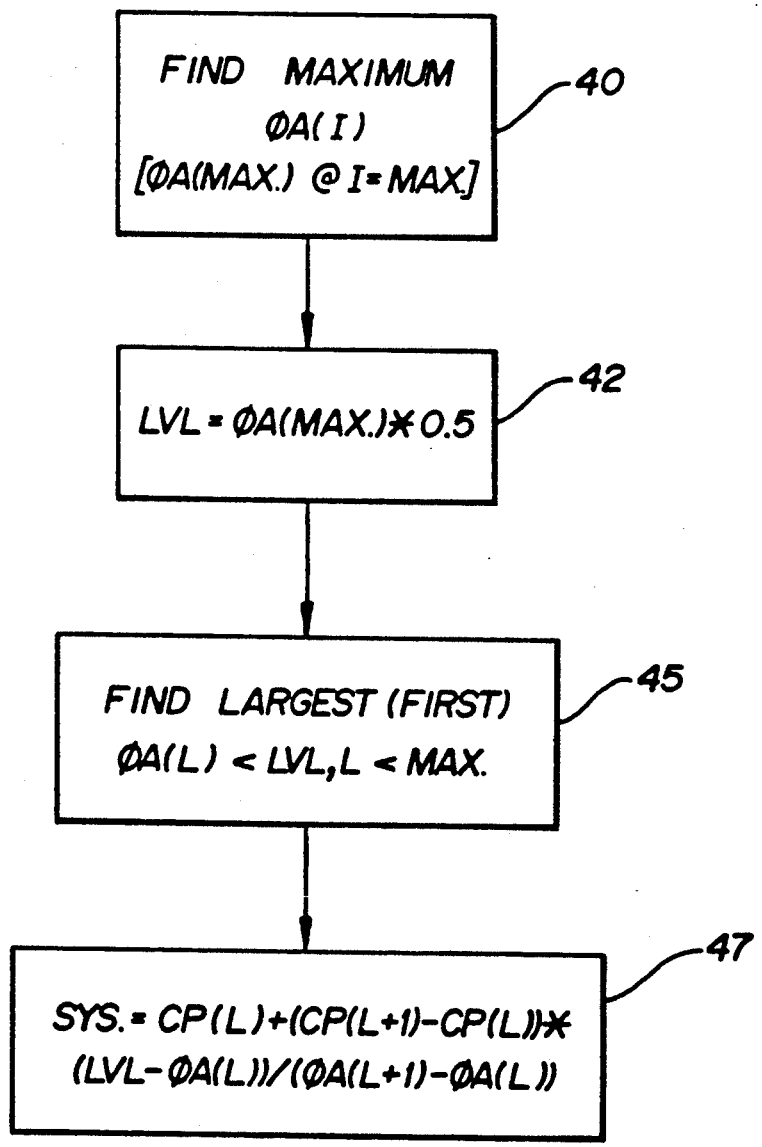
FIG-4 SYSTOLIC DETERMINATION

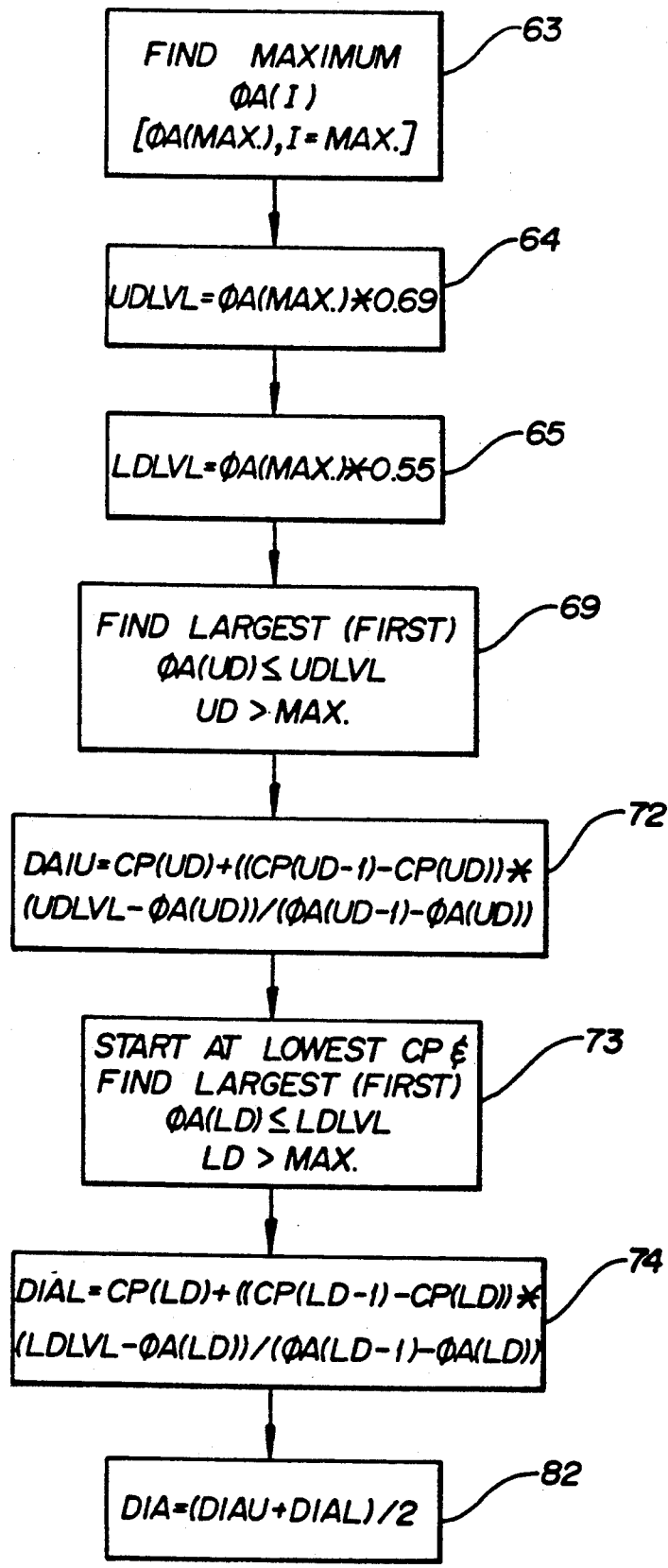
FIG-7  DIASTOLIC DETERMINATION

OSCILLOMETRIC BLOOD PRESSURE MONITOR AND METHOD EMPLOYING NON-UNIFORM PRESSURE DECREMENTING STEPS

This is a CIP application Ser. No. 751,840, filed on Jul. 5, 1985 now abandoned and a CIP of application Ser. No. 751,827 filed Jul. 5, 1985 now abandoned.

FIELD OF THE INVENTION

This invention relates to automated blood pressure measuring apparatus and, more particularly, to stored program controlled monitors employing the oscillometric method of detection characterized by data purification and enhanced systolic, diastolic and mean blood pressure determination.

CROSS REFERENCE TO RELATED APPLICATIONS

Reference is hereby made to the following concurrently filed co-pending commonly assigned patent applications: IMPROVED SPHYGMOMANOMETRIC CUFF PRESSURIZING SYSTEM. Ramsey et al. Ser. No. 751,835; IMPROVED AUTOMATED MEAN ARTERIAL BLOOD PRESSURE MONITOR WITH DATA ENHANCEMENT. Ramsey et al. Ser. No. 751,826; IMPROVED AUTOMATED DIASTOLIC BLOOD PRESSURE MONITOR WITH DATA ENHANCEMENT. Ramsey et al. Ser. No. 751,825.

BACKGROUND OF THE INVENTION

Automated blood pressure monitoring has rapidly become an accepted and, in many cases, essential aspect of human and veterinary treatment. Such monitors are now a conventional part of the patient environment in emergency rooms, intensive and critical care units, and in the operating theatre.

The so-called oscillometric method of measuring blood pressure is one of the most popular methods in commercially available systems. This method relies on measuring changes in arterial counterpressure, such as imposed by an inflatable cuff, which is controllably relaxed or inflated. In some cases the cuff pressure change is continuous, and in others it is incremental. In substantially all, a transducer monitors arterial counterpressure oscillations, and processing apparatus converts select parameters of these oscillations into blood pressure data.

Of particular interest with respect to the principles of the present invention are the concepts set forth in U.S. Pat. Nos. 4,360,029 and 4,394,034 to M. Ramsey, III, which are commonly assigned with the instant invention. The Ramsey patents derive from common parentage, the former including apparatus claims and the latter including method claims, their division having been made in response to a restriction requirement during the prosecution. Both patents, however, carry common disclosures of apparatus and methods for artifact rejection in oscillometric systems, which have been in practice in the commercially successful DINAMAP brand monitors, which are manufactured and marketed by Critikon, Inc., of Tampa, Fla., the assignee hereof. In accordance with the Ramsey patents, an inflatable cuff is suitably located on the limb of a patient, and is pumped up to a predetermined pressure. Thereupon, the cuff pressure is reduced in predetermined fixed decrements, at each level of which pressure fluctuations are monitored. These typically consist of a DC voltage with a small superimposed variational component caused by arterial blood pressure pulsations (referred to herein as "oscillatory complexes"). Therefore, after suitable filtering to reject the DC component and to provide amplification, pulse peak amplitudes above a given threshold are measured and stored. As the decrementing continues, the peak amplitudes will normally increase from a lower amount to a relative maximum, and thereafter will decrease. The lowest cuff pressure at which the oscillations have a maximum peak value is representative of mean arterial pressure. The cuff pressures obtaining when stored oscillatory complex pulse peak amplitudes bear predetermined fractional relationships with the largest stored peak corresponding to the subject's systolic and diastolic pressures.

The Ramsey patents devote considerable effort and disclosure to the rejection of artifact data to derive accurate blood pressure data. Indeed, as is apparent from FIG. 2 of the Ramsey patents, the most substantial portion of the measurement cycle (denominated "T3") is devoted to the execution of complex detection at the various pressure levels, measurement of signal peaks of true complexes, and processing those peaks in accordance with artifact rejection algorithms. Notwithstanding such efforts, the signal peak data collected sometimes incorporates data errors, i.e., a data pattern inconsistent with the above described typical physiological response pattern of a subject as the artery occluding cuff pressure monotonically decreases.

Further, in a contemporaneous invention (see M. Ramsey III, et al patent application Ser. No. 751,835 for "OSCILLOMETRIC BLOOD PRESSURE MONITOR EMPLOYING NON-UNIFORM PRESSURE DECREMENTING STEPS" filed on even date herewith, the disclosure of which is incorporated herein by reference) oscillometric blood pressure measurements are effected with non-uniform cuff pressure-dependent pressure decrements between successive oscillatory complex peak measuring intervals. Such a method of effecting oscillometric blood pressure measurements is facilitated by systolic, diastolic and mean blood pressure determining algorithms not heretofore employed.

It is an object of the present invention to provide improved oscillometric blood pressure determining apparatus and methodology.

More specifically, it is an object of the present invention to purify the osciilatory complex peak amplitude data ensemble employed for blood pressure determination.

Yet another object of the present invention is the provision of improved algorithms, methodology and apparatus for determining systolic, diastolic and mean arterial blood pressure.

SUMMARY OF THE INVENTION

A blood pressure cuff is applied about a subject's artery, and inflated above the systolic level thus fully occluding the artery for a full heart cycle. The cuff pressure is thereafter reduced to permit an increasing flow through the progressively less occluded artery, and a measure of the peak amplitudes of the successively encountered oscillatory complexes stored in memory. Also retained is the cuff pressure obtaining for each stored complex peak.

In accordance with varying aspects of the present invention, the stored complex peak-representing data set is corrected for aberrations; and improved data processing operates on the stored (and advantageously corrected) pulse peak data and the corresponding cuff pressure information to determine the subject's systolic, diastolic and mean arterial pressure.

DESCRIPTION OF THE DRAWINGS

The above and other objects and features of the present invention will be realized from the following detailed discussion of a specific, illustrative embodiment thereof, presented hereinbelow in conjunction with the accompanying drawing in which:

FIG. 4 is a program flow chart for the systolic blood pressure measurement typified in FIG. 3;

FIG. 7 is a program flow chart illustrating the diastolic blood pressure measurement typified by FIG. 6;

BEST MODE FOR CARRYING OUT THE INVENTION

Figure 1:
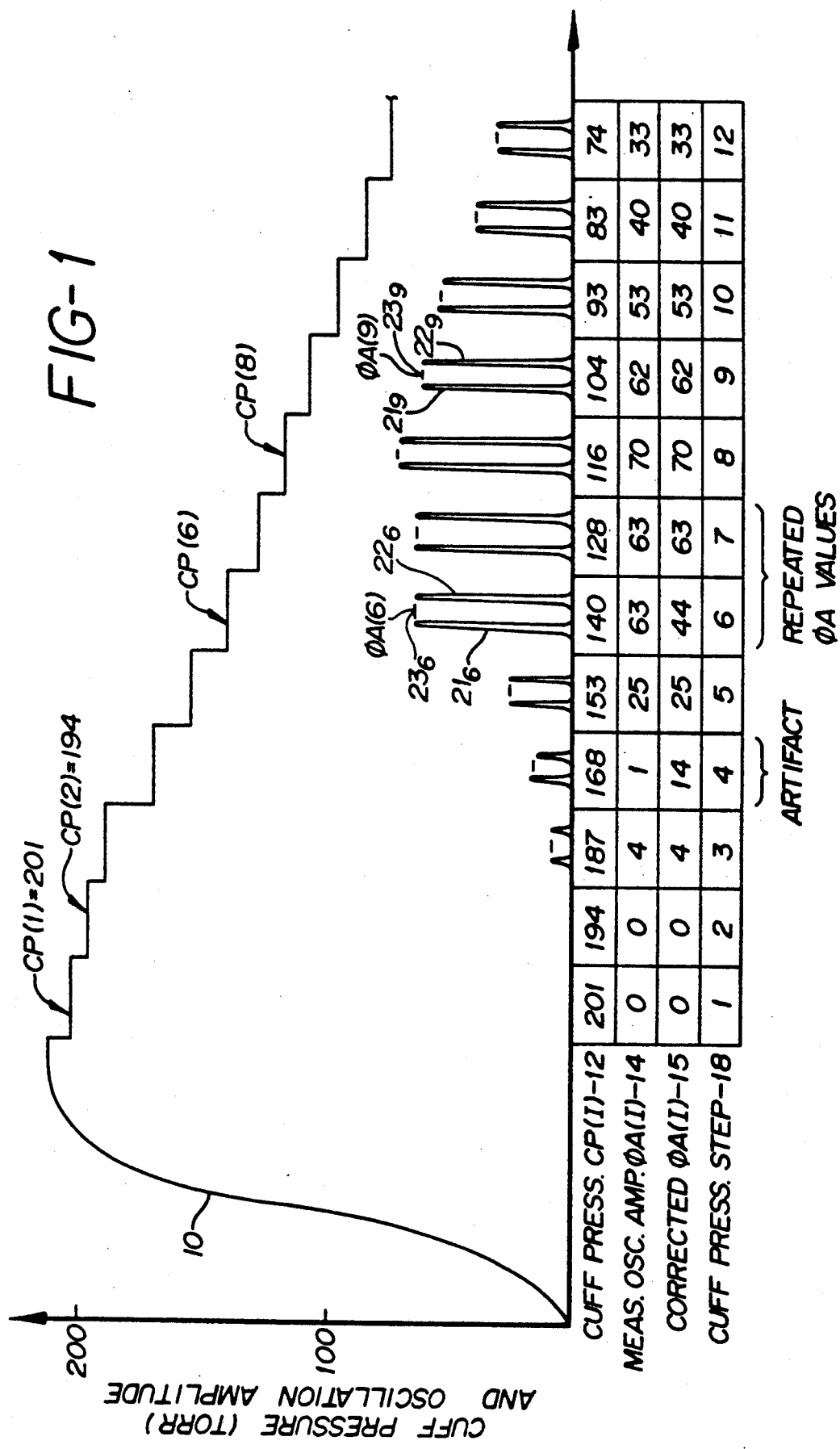
FIG. 1 is a timing diagram illustrating data generation and correction during an illustrative measurement cycle for oscillometric blood pressure determination in accordance with the principles of the present invention.

U.S. Pat. Nos. 4,360,029 and 4,349,034, each to Maynard Ramsey III, and Maynard Ramsey, III et al U.S. Pat. No. 4,543,962 for "IMPROVED METHOD OF AUTOMATED BLOOD PRESSURE DETECTION" issued Oct. 1, 1985 are incorporated herein by reference, as is the aforementioned co-filed Ramsey III et al application. These patents and patent applications describe in detail the basic oscillometric method of measuring blood pressure forming a background and a starting point for the instant invention.

To review only briefly, an artery-occluding cuff is disposed on the subject, e.g., about a subject's upper arm over the brachial artery. At the inception of a measuring cycle, the cuff is inflated to a pressure which fully occludes the brachial artery, i.e., prevents blood from flowing therethrough at any point in the heart cycle. The cuff is then progressively deflated, as in discrete steps. A pressure transducer is coupled to the internal cuff pressure and provides an analog signal characterizing the blood pressure oscillatory complexes when they begin to occur (i.e., when the maximum heart pressure corresponding to contraction of the heart's left ventricle exceeds the instantaneously obtaining artery-occluding cuff pressure). The peak values of the complex signals are determined in hardware or software.

As the measurement cycle progresses, the peak amplitude of the blood pressure complexes generally become monotonically larger to a maximum and then become monotonically smaller as the cuff pressure continues toward deflation. The peak amplitude of the cuff pressure oscillation complexes, and the corresponding occluding-cuff pressure values are retained in computer memory. The aforementioned Ramsey patents and patent applications illustrate previously employed algorithms for processing the stored blood pressure complex peak values and concomitant pressure values to yield the subject's mean arterial pressure. These patents and applications also furnish detailed procedures for measuring oscillatory complex peaks; procedures for testing complexes and rejecting bad data associated with measurement-impeding artifacts (such as motion) during a measuring cycle, and the like.

The oscillometric blood pressure measurements as typified by the aforementioned Ramsey disclosures are effected under stored program control, as via a microprocessor operative in conjunction with a program containing read only memory (ROM or PROM), and a variable content random access memory (RAM) which stores the cuff pressures, oscillatory complex peak amplitudes, and other processing operand variables. The microprocessor receives the cuff pressure readings generated by the pressure transducer, for example as processed by a peak detector, amplifier and analog-to-digital converter, and supplies all output control signals required, e.g., to open and close one or more cuff deflating valves.

The oscillometric method above described and more fully discussed in the aforementioned Ramsey patents and applications may be conducted with several variations. Thus, for example, the cuff may be inflated directly by an air pump; and deflated in fixed, discrete steps under microprocessor control. Alternatively, the cuff may be principally or entirely inflated by the pressurized contents of an air reservoir; and/or deflation may proceed in variable, cuff pressure-dependent steps via selected one or ones of plural deflating valves. These latter alternatives achieve the desideratum of condensing the time required for a composite measurement cycle of operation.

Also, there are alternative procedures for measuring the oscillatory complex peak amplitude at any prevailing cuff pressure. In one mode heretofore employed, plural (e.g., two) complex peaks are measured at each cuff pressure step during cuff deflation, and their average used as the peak value. Since the peaks should be approximately equal, any marked disparity (e.g., >20%) signals that some artifact error occurred and the data is rejected. In a fast ("stat") mode, after several intervals of qualifying (close or equal peak values) companion complexes are detected to develop measurement confidence, only one pulse is required during succeeding cuff deflation intervals thus speeding the composite measurement period. Please see in this later regard the aforementioned application filed Jul. 9, 1984.

As alluded to above, it is sometimes the case when blood pressure complexes are being examined for peak amplitude at any occluding pressure level that improper data is developed. There are varying causes for such aberrations. Perhaps the most common is spurious motion by the subject which generates an inadvertent pressure impulse in the cuff which is sensed by the pressure transducer which may be then incorrectly reflected in the blood pressure measurement. Other causes include varying sources of interfering electrical noise or internal cardiac or respiratory changes in the subject. When a false complex peak amplitude value is generated, it is discarded by the composite measuring apparatus and a discard-signalling value (e.g., +1) retained in its place in memory.

A second form of spurious data occurs when the pattern of stored pulse peak values departs from the physiologically mandated sequence of values which progressively increase to a peak and then progressively decrease.

Attention will now be directed to data processing under stored program control for purifying the data collected by the above-described blood pressure measuring apparatus. Further, specific illustrative efficient algorithms are discussed for in fact determining the subject's systolic, diastolic and mean arterial blood pressures. Such data processing may be effected on any computing equipment, preferably digital microprocessors such as commercially available from a number of vendors. The program instructions and sequences presented below are for illustrative purposes only. Such instructions may in fact be implemented in any of diverse program languages and sequences readily apparent to those skilled in the art. In the signal processing below discussed, processing variables have the following significance:

| I. Variables Employed For All Data Processing Below Discussed | |
|---|---|
| Variable | Functional Quantity Represented |
| CP(I) | The cuff pressure, measured by the transducer pneumatically coupled to the artery occluding cuff, obtaining during the i-th deflation step. CP(I) is an indexed array, i.e., there exists a plurality of values for CP(I) characterizing each of the i deflation steps. |
| $\Phi A(I)$ | The peak amplitude of the oscillometric oscillation (i.e., the complex peak amplitude) occurring at the i-th step. Where multiple complexes are measured during each prevailing deflation pressure. $\Phi A(I)$ is the average of two (or more) peak amplitudes during the i-th step. $\Phi A(I)$ is an indexed array. |
| $\Phi A(MAX)$ | The peak value of the array of averaged oscillatory blood pressure complex amplitudes. |
| MAX | The time interval when the peak complex $\Phi A(MAX)$ occurred. |

| II. Variables Specific To Systolic Pressure Measurement | |
|---|---|
| Variable | Functional Quantity Represented |
| LVL | An intermediate processing variable representing a predetermined fraction of $\Phi A(MAX)$. |
| SYS | The subject's measured systolic pressure. |

| Variable | Functional Quantity Represented |
|---|---|
| III. Diastolic Pressure Variables | |
| UDLVL and LDLVL | Intermediate processing variables each representing a different fraction of $\Phi A(MAX)$. |
| DIAU, DIAL | Intermediate processing variables representing upper and lower interpolated diastolic pressure computational variables. |
| DIA | The subject's measured diastolic pressure. |
| IV. Mean Arterial Pressure Processing Variables | |
| AMP | The complex pulse peak for the deflation interval following that for which the pressure oscillation amplitude was the maximum. |
| MAPL | An intermediate processing variable employed in the final mean arterial pressure computation. |
| MAP | The subject's mean arterial blood pressure. |

Turning now to FIG. 1, there is depicted wave forms with associated data characterizing the generation of data for an oscillatory blood pressure measurement—and purging (overcoming) bad data constituents. In accordance with the above discussion, the cuff artery occluding pressure for a measurement cycle, as measured by the cuff-associated transducer, is characterized by a wave form 10. The cuff pressure rapidly increases to a maximum above the subject's systolic pressure, and is then deflated in a sequence of steps to a point below the diastolic pressure. The sequence of cuff deflation steps is indicated by the time interval signalling digits 1,2, ..., (lowest row 18 in the data table portion of FIG. 1). The internal pressure characterizing the cuff pressure at each step i is given by the data array CP(1),CP(2), ... (upper data table row 12).

Each step (time interval) is made sufficiently long to include at least two heart beats. Accordingly, at least two cuff pressure complex pulses 21 and 22 are measured during each interval after such pulses begin. Legend have been applied to pulses occurring during deflation steps 6 and 9 to avoid clutter and loss of clarity in FIG. 1. No pulses are measured during the first and second pressure steps (time intervals), it being assumed that the cuff pressure [CP(1)=201 Torr., and CP(2)=194 Torr.] are sufficient during these periods to obviate blood flow through the subject's artery for the full heart cycle. During the following intervals 3,4 ..., two oscillometric complex pulses 21 and 22 are generated and measured, the two pulses having an average peak amplitude 23 (the processor variable array value initially stored in $\Phi A(I)$). The measured oscillation amplitude array ($\Phi A(I)$) is shown in the second row 14 of the FIG. 1 data table for each time interval.

As above noted, assuming a perfect measurement, the oscillation pressure amplitude $\Phi A(I)$ data row would not contain any +1 values which signify an impeded measurement. Further, the data pattern in the second row of the data table for the oscillation amplitudes would exhibit a pattern of successively increasing numbers to a peak value, followed by progressively decreasing values—all without adjacent equal $\Phi A(I)$ values. To the extent that any $\Phi A(I)=1$ values are stored, or to the extent that the progressively increasing/decreasing pattern does not obtain, the data processing in accordance with the instant invention functions to compute appropriate corrected $\Phi A(I)$ values (the third data table row 15 in FIG. 1) for the oscillation amplitude entries requiring correction.

In overview, where any $\Phi A(I)=1$ values exist, they are replaced by the average value of the oscillation amplitude in the two contiguous storage cells, i.e., $$\Phi A(I)=(\Phi A(I-1)+\Phi A(I+1))/2. \qquad 1$$

Correspondingly, where two contiguous oscillation amplitudes have the proscribed equal values, the first of the contiguous equal pair is replaced by the average of the amplitudes of the complex peaks measured at the next lower and next higher occluding cuff pressures. See, for example, Eq. 1 and, more particularly, the comparable relationship in functional block 30 of FIG. 2.

Figure 2:
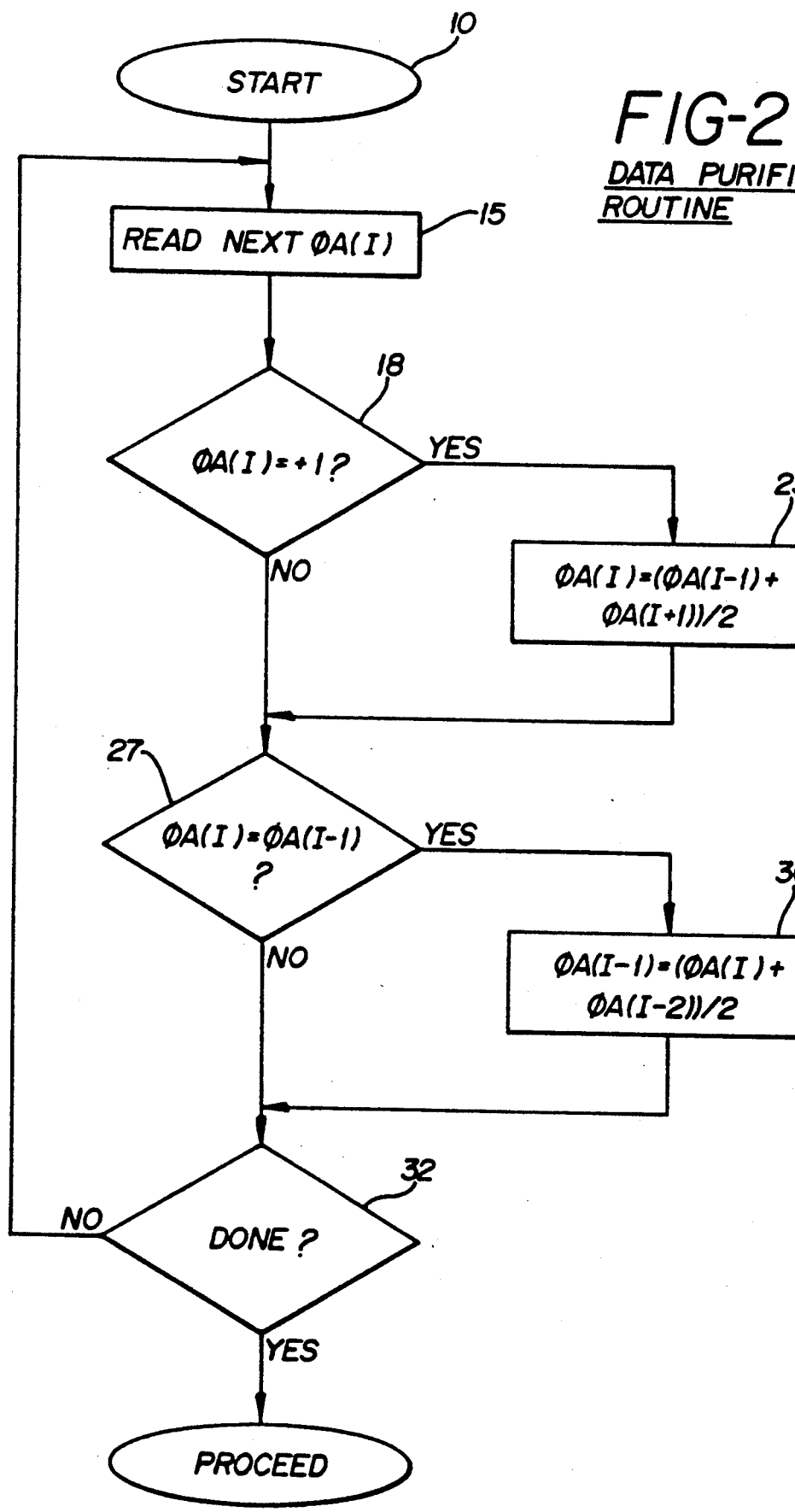
FIG. 2 is a flow chart illustrating data purification for improved oscillometric blood pressure determination.

Data flow effecting the data purification algorithm above-discussed is set forth in the program flow chart of FIG. 2. FIG. 2 operates on the measured average oscillation amplitudes (the second data table row 14 in FIG. 1) and generates the corrected $\Phi A(I)$ values shown in the third row 15 of FIG. 1. To this end, proceeding from a start block 10 (FIG. 2), step 15 reads the next value $\Phi A(I)$ (proceeding toward the right along the FIG. 1 data table row 14) and test 18 determines whether the value stored in $\Phi A(I)$ equals the error-signalling value +1. If as is the usual case it does not (indicating that the value measured was presumptively free of artifacts and the like), control passes to equality test 27. However, if the contents of $\Phi A(I)$ did equal +1 ("YES" branch of test 18), functional block 23 implements Eq. 1, i.e., replaces the +1 former contents of memory cell $\Phi A(I)$ corresponding to cuff pressure $CP(I)$ with the average value of the oscillation amplitude measured at the next lower ($\Phi A(I-1)$) and next higher non-plus one ($\Phi A(I+1)$) deflation steps. The processing steps 18 and 23 thus purge the measured pressure peak amplitude storage contents (the second row of the FIG. 1 data table) of all +1 values, replacing these by the average value of the measurements made during immediately adjacent deflation steps (corrected $\Phi A(I)$ contents being illustrated in row 15).

Test 27 next examines the current operand $\Phi A(I)$ for the proscribed equality with the previous value $\Phi A(I-1)$. If, as is normally the case, the contents of $\Phi A(I)$ and $\Phi A(I-1)$ differ ("NO" branch from test 27), processing flows to test 32 to determine whether each of the N elements of $\Phi A(I)$ have been processed. If they have not, control returns to block 15 to read in and process the next $\Phi A(I)$ element of the array in the third row 15 of the FIG. 1 data table. When all elements have been processed, control exits from the FIG. 2 data purification routine to data processing point 33 to proceed with the next (unrelated) task for the microprocessor.

If a data error has occurred ("YES" output of test 27 signalling that a data value $\Phi A(I)$ equaled the previous value), control passes to step 30 which replaces the assumed erroneous element $\Phi A(I-1)$—(the value which should differ from $\Phi A(I)$ but did not) with the average of the two immediately contiguous elements as by $$\Phi A(I-1)=(\Phi A(I)+\Phi A(I-2))/2. \qquad 2$$

Accordingly, the data purification routine depicted in FIG. 2 and above-discussed replaces all error reading signifying $\Phi A(I)=1$ values with an interpolated estimated value; and purges the data table row 14 $\Phi A(I)$ array of data of any contiguous equal values. The corrected set of $\Phi A(I)$ is shown in the third row 15 of the FIG. 1 data table. Thus, for example, the oscillation amplitude value during the cuff pressure step (time interval) "4" is corrected from the error-signalling +1 value to a peak amplitude 14, representing the average of measurements 4 and 25 at cuff pressures 187 Torr. and 153 Torr. during the immediately contiguous time intervals 3 and 5. Similarly, the first (pressure step 6) of two equal measured oscillation amplitude pulses of value 63 during periods 6 and 7, corresponding to occluding cuff pressures of 140 Torr. and 128 Torr., is corrected to a value of 44 representing the average of the contiguous measured amplitudes of 63 and 25 units.

The corrected array $\Phi A(I)$ as represented by the third row 15 in FIG. 1 thus comprises value from which each of the systolic, diastolic and mean arterial blood pressures may be determined either in accordance with the improved algorithms below discussed or employing the algorithms of the above referenced patents and patent applications. The data purification above discussed provides more accurate measurements than was heretofore the case; and also permits blood pressures to be determined more quickly, obviating the need for repeated deflation steps when unacceptable artifact or noise corrupted data is sensed.

Figure 3:
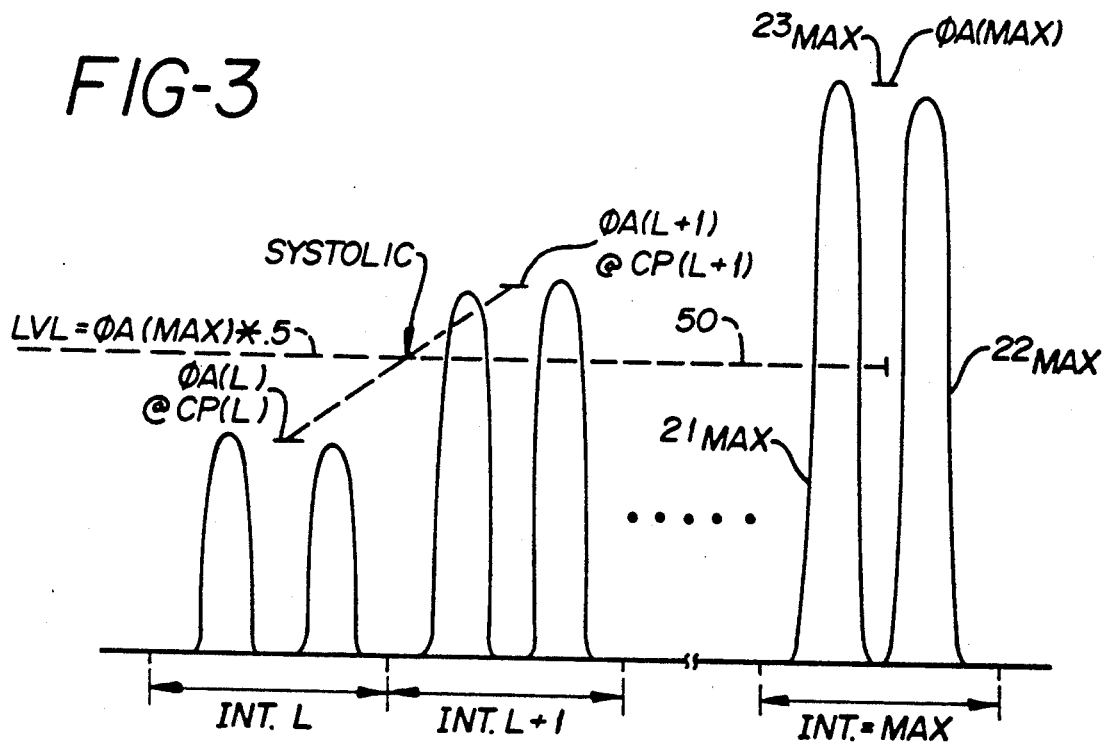
FIG. 3 depicts oscillation amplitude processing for a systolic blood pressure measurement in accordance with the present invention.

Attention will now be shifted to the particular method pursuant to which the stored cuff pressure $CP(I)$ and corrected blood pressure peak value $\Phi A(I)$ information in the first and third data rows of FIG. 1 is employed in accordance with other aspects of the present invention to measure a subject's systolic, diastolic and mean arterial blood pressures.

pulse complex wave form processing typifying systolic blood pressure determination is illustrated in FIG. 3, and a flow chart for the underlying data processing is set forth in FIG. 4. In overview, systolic pressure is determined by:

(a) Finding the amplitude ($\Phi A(MAX)$) of the largest blood pressure oscillatory complex (which occurs at the time interval MAX);

(b) Finding an amplitude level (LVL) equal to a predetermined fraction of the peak value $\Phi A(MAX)$. We have found a value of 0.5 to be satisfactory for normal processing with something less (e.g., 0.45) for stat (rapid deflation and/or single pulse) operation;

(c) Examining the corrected oscillation amplitude ($\Phi A(I)$) values (third row 15 in the FIG. 1 data table) starting at the MAX interval and proceeding toward the higher cuff pressure direction (i.e., to the left in FIGS. 1 and 3) to find the two contiguous oscillation amplitudes for which $$\Phi A(L) \leq MAX*0.5 < \Phi A(L+1); \qquad 3$$

Figure 5:
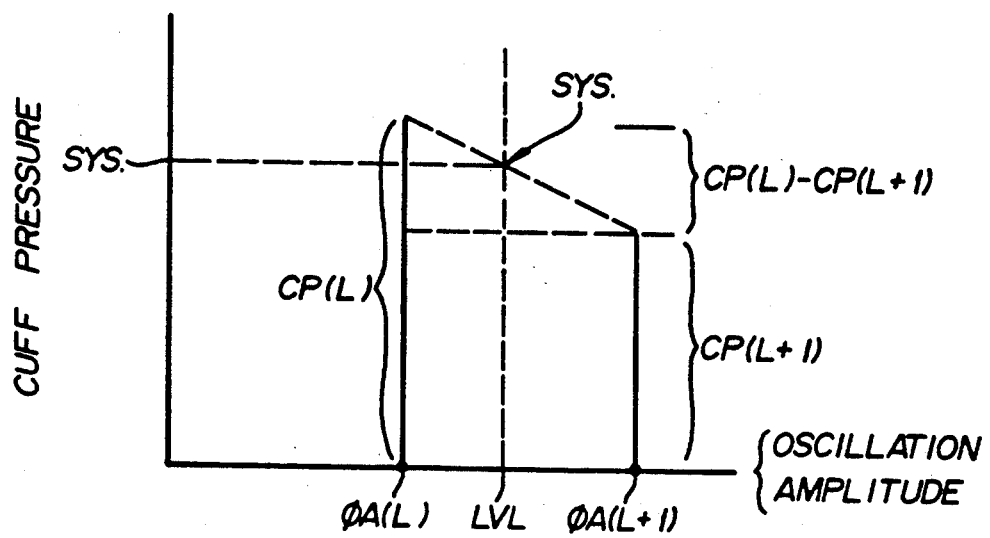
FIG. 5 illustrates blood pressure interpolation for the processing mode of FIGS. 3 and 4 (and by analogy for FIGS. 6-9 as well)

(d) Computing the interpolated cuff pressure (between $CP(L)$ and $CP(L+1)$) assuming a linear variance in oscillation amplitude and cuff pressure between the intervals L and L+1. This per se well known linear trapezoidal interpolation is graphically depicted in FIG. 5, The interpolated cuff pressure directly corresponds to the subject's systolic blood pressure (SYS). Expanding upon the systolic pressure determining methodology set forth above, the cuff pressure interval I=MAX when the largest oscillation amplitude peak occurs is determined in any per se well known manner, (step 40 of the FIG. 4 flow chart corresponding to the interval MAX in FIG. 3).

Thus, for example, the following schematic BASIC sequence will suffice as illustrative to find the interval MAX:

| | |
|---|---|
| ΦAMAX=ΦA(1) | 4 |
| MAX=1 | 5 |
| FOR K=2 TO N | 6 |
| IF ΦA(K)<ΦAMAX GOTO 70 | 7 |
| ΦAMAX=ΦA(K) | 8 |
| MAX=K | 9 |
| 70 NEXT K | 10 |

In brief, Equations 4 and 5 make an initial assumption that the peak value occurred during the first interval and load a provisional peak value storing variable OAMAX with the value ΦA(1). For an assumed N-time interval measurement, the loop between Equations 6 and 10 sequentially examines every element of the ΦA(I) array from 2 to N, updating ΦAMAX only when the value ΦA(K)—(K being the loop index) exceeds the previously assumed ΦAMAX value. When the processing exits from the loop following instruction 70 in Equation 10 the variable MAX contains the value of I such that ΦA(MAX) is the largest value in the array.

The next following step 42 sets a variable LVL equal to the predetermined fraction of the peak amplitude ΦA(MAX) as by $$LVL = \Phi A(MAX) * 0.5. \qquad 11$$

The value LVL is shown by the dashed line 50 in FIG. 3.

The next following operation 45 finds the first time interval (L) preceding MAX for which the oscillation amplitude peak is less than LVL, i.e., less than one-half of the peak value ΦA(MAX). thereby finding the two contiguous values (L, L+1) having peak amplitudes which bound the value in LVL. Algorithms for conducting such a search are well known to those skilled in the art, e.g.,

| | |
|---|---|
| FOR J=1 TO MAX | 12 |
| IF (ΦA(MAX-J)-LVL)<0 GOTO 140 | 13 |
| NEXT J | 14 |
| 140 L=MAX-J | 15 |

Equations 12–15 simply comprise a DO or FOR-NEXT loop progressing from MAX-1 toward L=1, exiting when the first sub-LVL value is obtained. The appropriate interval identification (MAX-J) is stored in the variable location L.

Finally, the value of the systolic pressure is estimated by assuming a linear variation in cuff pressure between the values CP(L) and CP(L+1), and a linear variation between the corresponding oscillation amplitude ΦA(L) and ΦA(L+1). Thus, in accordance with the per se well known trapezoidal interpolation equation, the systolic pressure SYS may be determined (step 47 of FIG. 4) by $$SYS = CP(L) + \frac{(CP(L+1) - CP(L))*((LVL) - \Phi A(L))}{\Phi A(L+1) - \Phi A(L)} \qquad \text{Eq. 16}$$

To illustrate employing the data of FIG. 1, 50% of the peak amplitude (70) is 35, and thus the pulse complex measurements of time intervals 5 and 6 are selected for systolic pressure computation. The Eq. 16 software interpolation implementation yields:

$$SYS = 153 + ((140 - 153) \times (35 - 25)/(44 - 25)); \qquad \text{Eq. 17}$$
$$= 149 \text{ Torr.} \qquad \text{Eq. 18}$$

assuming three significant figures.

Figure 6:
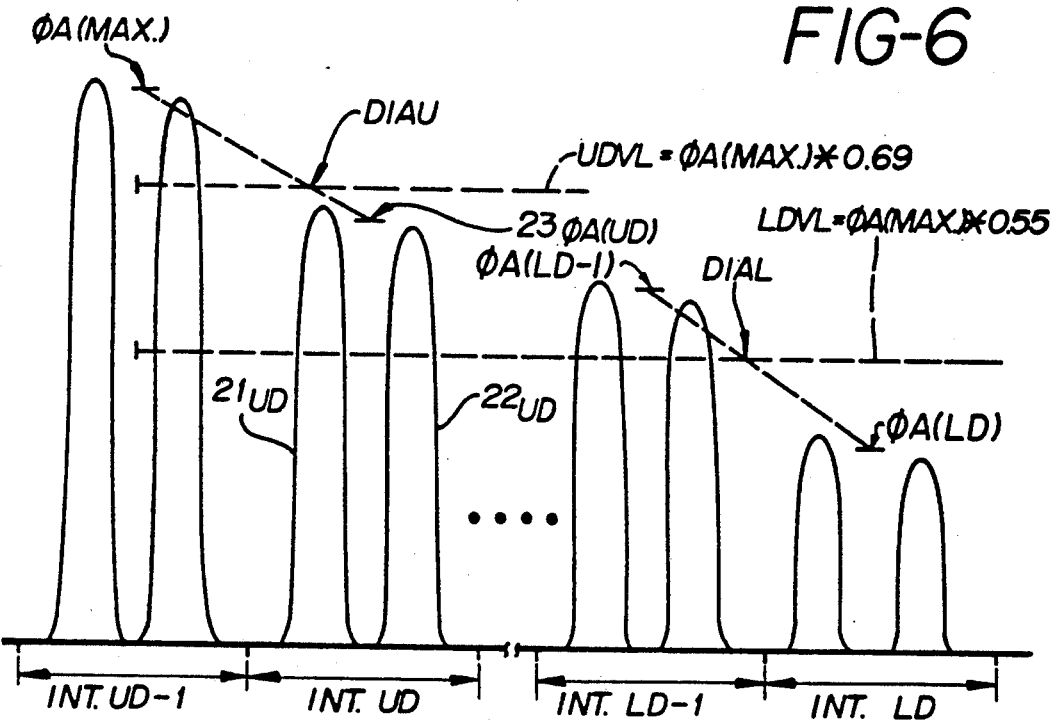
FIG. 6 depicts oscillatory complex measuring wave forms illustrating diastolic blood pressure determination in accordance with the present invention.

Pulse complex wave form processing characterizing diastolic blood pressure determination is illustrated in FIG. 6; and a flow chart for the underlying diastolic data processing algorithm is depicted in FIG. 7. In overview, diastolic pressure is determined by:

(a) the amplitude (ΦA(MAX)) of the complex (which occurs at the time interval MAX);

(b) Finding an amplitude level (UDLVL) equal to a first predetermined fraction of the peak value ΦA(MAX). We have found a value of 0.69 to be satisfactory for normal processing and 0.72 for rapid ("stat") processing;

(c) Examining the corrected oscillation amplitude (ΦA(I)) buffer 15 (FIG. 1) starting at the MAX interval and proceeding toward the lower cuff pressure direction (i.e. to the right in FIGS. 1 and 6) to find the two contiguous oscillation amplitudes for which $$\Phi A(UD) \leq MAX*0.69 \leq \Phi A(UD-1); \qquad 19$$

(d) Finding the interpolated cuff pressure (between CP(UD-1) and CP(UD)) assuming a linear variation in oscillation amplitude and cuff pressure between the intervals UD-1 and UD (processing variable DIAU in FIG. 7);

(e) Examining the stored ΦA(I) oscillation amplitude values at pressures starting at the lowest CP measured for a contiguous pair bounding the peak amplitude ΦA(MAX) multiplied by a second factor lower than the first factor (e.g., 0.55), i.e., where $$\Phi A(LD) \leq MAX*0.55 \leq \Phi(LD-1); \qquad 20$$

(f) Computing the interpolated cuff pressure between CP(LD) and CP(LD-1) corresponding to MAX times the 0.55 factor. This lower interpolated cuff pressure is associated with the variable designation DIAL; and (g) Determining the subject's diastolic pressure (DIA) as the average of the upper and lower interpolated values DIAU and DIAL, i.e., $$DIA = (DIAU + DIAL)/2 \qquad 21$$

The above-described procedure is illustrated in the blood pressure complex depiction of FIG. 6 and the FIG. 7 flow chart. The peak ΦA(MAX) is first located as by the processing of Equations 4–10. The upper and lower peak amplitude fractions DIAU and DIAL are next determined (steps 64 and 65 of FIG. 7 corresponding to the labeled horizontal dash lines in FIG. 6). Step 69 then finds the first time interval (UD) following MAX at which the peak amplitude ΦA(UD) is lower than the value stored in DIAU (as by processing analogous to that of Equations 12 through 15 replacing "MAX−J" with "MAX+J"). Thereafter, step 72 performs the trapezoidal interpolation analogous to that of FIG. 5, determining the cuff pressure (DIAU) corresponding to the UDLVL complex amplitude value. It is observed that the time interval UD−1 coincides with the interval MAX when the peak complex value occurred since, for the data case illustrated, the first pulse complex following MAX less than 0.69×ΦA(MAX) occurred in the next time interval MAX+1.

The functional steps 73 and 74 of FIG. 7 perform in a manner directly analogous to operations 69 and 72, locating the cuff pressure DIAL by interpolation for the intervals when the peak complex amplitudes bound the LDLVL value equal ΦA(MAX) times 0.55. This latter search is conducted from ΦA(i) at the lowest CP, then working toward higher CP's. Finally, the subject's diastolic pressure (DIA) is computed as the average of the contents stored in DIAU and DIAL (step 82).

To illustrate with a numerical example, again employing the data portion of FIG. 1, $$DIAU = 83 + ((93-83) \times (48-40))/(40-53) = 71. \quad 22$$

$$DIAL = 74 + (83-74) \times (38-33))/(33-40) = 67. \quad 23$$

$$DIA = (71+67)/2 = 69. \quad 24$$

Figure 8:
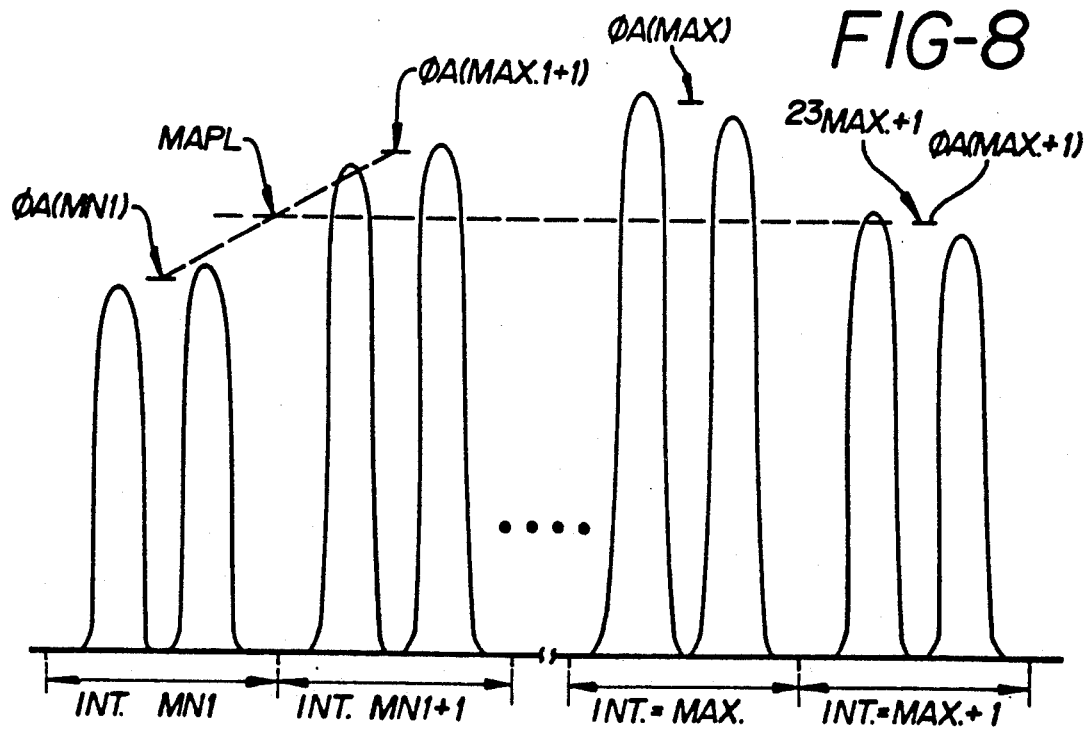
FIG. 8 is a timing diagram depicting oscillatory complex peak amplitude processing for mean arterial pressure measurements in accordance with the present invention.
Figure 9:
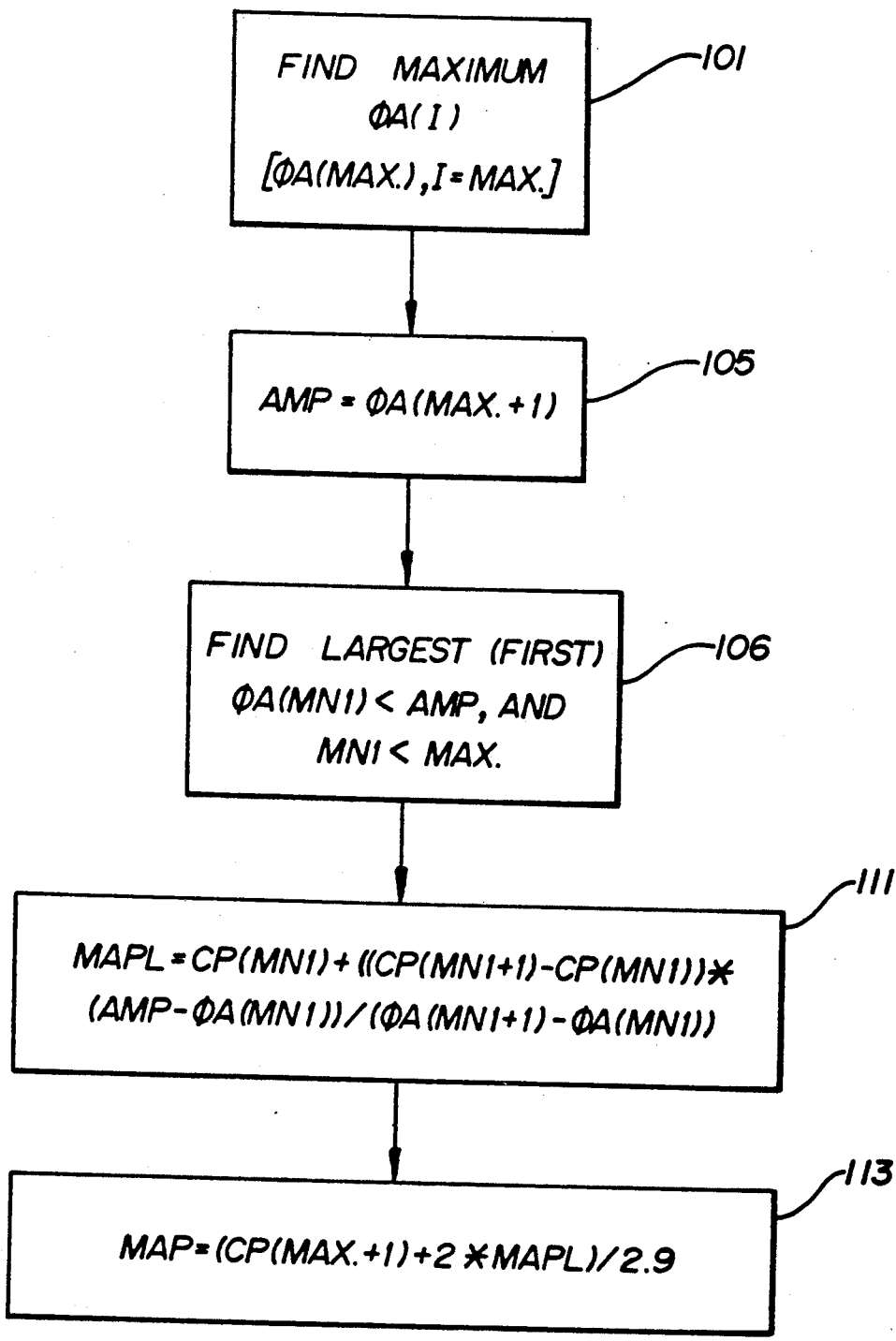
FIG. 9 is a program flow chart illustrating the mean arterial pressure determination typified by FIG. 8.

Finally, wave form processing illustrating mean arterial blood pressure measurement is shown in FIG. 8, and in flow chart form for the corresponding data processing in FIG. 9. In summary, mean arterial pressure is determined by:

(a) Finding the amplitude (ΦA(MAX)) of the largest blood complex (which occurs at the time interval MAX);

(b) Examining the cuff pressure values in the corrected register 15 (FIG. 1) for the interval MNl yielding the first oscillation amplitude less than ΦA(MAX+1), i.e., the first cuff pressure to the left of the interval MAX which was less than the complex peak amplitude ΦA(MAX+1) occurring in the first interval following the time MAX. This satisfies the relationship $$\Phi A(MNl) \leq \Phi A(MAX+1) \leq \Phi A(MNl+1); \quad 25$$

(c) An interpolation is then conducted between the intervals MNl and MNl+1 for a cuff pressure MAPL corresponding to the oscillation amplitude value ΦA(MAX+1); and (d) Finally, the mean arterial pressure (MAP) is determined by a weighting of the cuff pressures CP(MAX+1) and MAPL, as by $$MAP = (CP(MAX+1) + (2 \cdot MAPL))/2.9. \quad 26$$

The denominator (2.9 in Eq. 26) may be somewhat lower for operation in a "stat" mode, e.g., 2.85.

The above-discussed algorithm for determining mean arterial pressure is illustrated in FIGS. 8 and 9. Step 1011 (FIG. 9) finds the peak interval MAX (for example, by execution comparable to Equations 4-10). A processing variable AMP is set equal to the peak value ΦA(MAX+1) of the complex following the interval MAX (step 105) and the interval MNl is next determined (step 106) as the first occurring complex less than the value AMP (i.e., ΦA(MAX+1)) to the left of time MAX in FIG. 8 (e.g., by processing comparable to Equations 12-15). An interpolation is then conducted to find the point MAPL (FIG. 8; step 1111 in FIG. 9) and the final processing operation 1131 finds the subject's mean arterial pressure by implementing Equation 26.

To again illustrate by numerical example from the FIG. 1 data $$MAPL = 140 + ((128-140) \times (62-44))/(63-44) = 129 \quad 27$$

$$MAP = (104 + 2 \cdot 129)/2.9 = 124 \quad 28$$

The foregoing discussion has thus demonstrated that measured data may be enhanced by replacing data lost through measurement artifacts or the like or deviations from a proper data pattern by approximated values. Specific data processing algorithms were presented and discussed for the computation of a subject's measured systolic, diastolic and mean arterial blood pressures.

Figure 10:
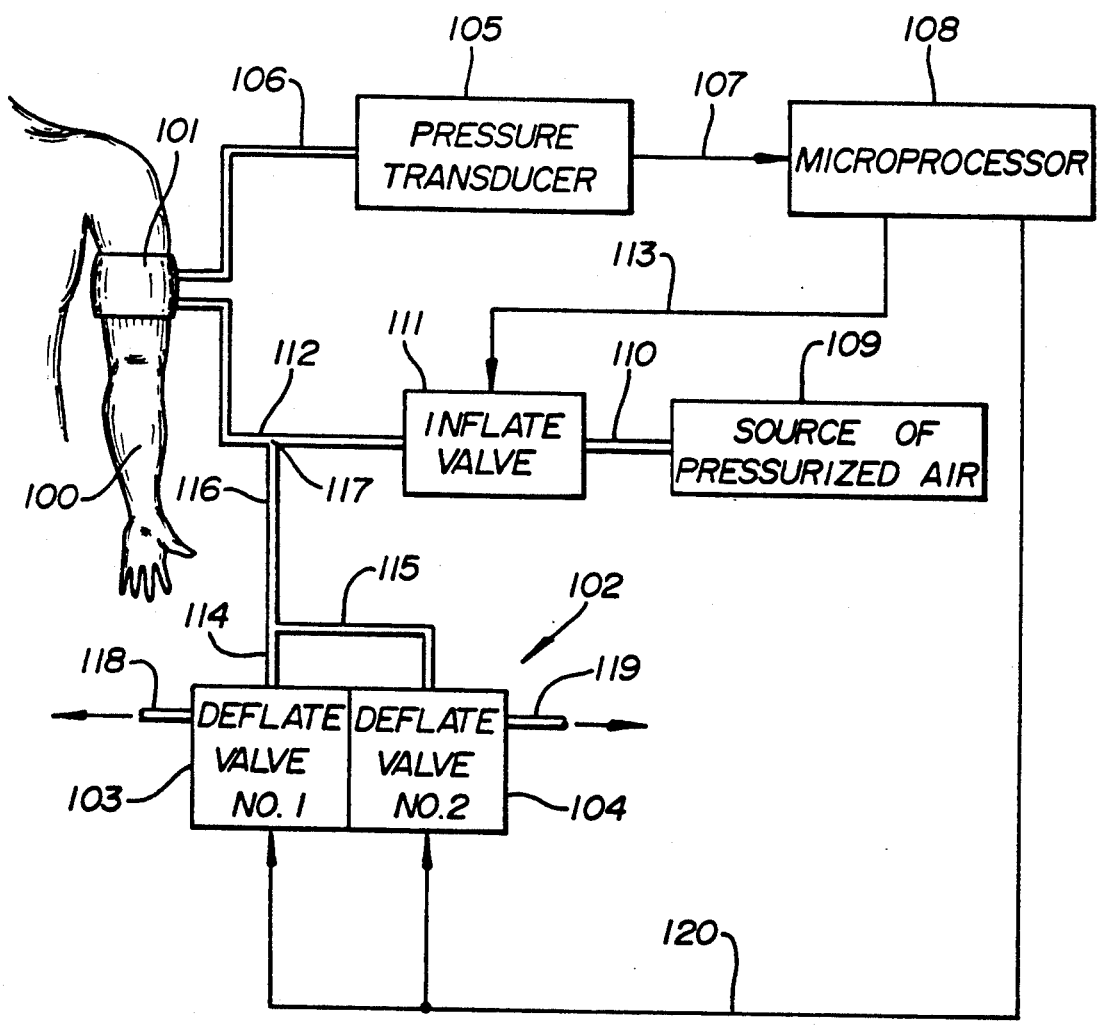
FIG. 10 is a schematic representation of a system and the basic components embodying the present invention.

Referring to FIG. 10 herein, there is shown an illustrative embodiment of the principles of the present invention. The arm 100 of a human subject is shown wearing a conventional flexible inflatable and deflatable cuff 101 for occluding the brachial artery when fully inflated. As the cuff 101 is deflated in a manner to be described further below, via air venting deflate valve apparatus 102 consisting of first and second deflate valves 103 and 104, the arterial occlusion is gradually relieved. A pressure transducer 105 is coupled by a duct 106 to the cuff 101 and senses the pressure therein. In accordance with conventional oscillometric techniques pressure oscillations in the artery are sensed by changes in the counterpressure of the cuff 101, and in turn by the transducer 105, there to be converted to an electrical signal and coupled over path 107 to a microprocessor or other controller 108. From the standpoint of the principles of the present invention, the processing of the signals from pressure transducer 105 by the microprocessor 108 to produce blood pressure data, and optionally to reject artifact data can be conducted in accordance with the prior art for example in accordance with the teachings of the above-referenced Ramsey '029 patent.

A source of pressurized air 109 is shown connected via a duct 110 through an inflate valve 111 and a duct 112 to the pressure cuff 101. The inflate valve 111 is electrically controlled through a connection 113 from the microprocessor 108.

The deflate valve apparatus 102 has its valves 103 and 101 connected by respective ducts 114 and 115 to a junction with duct 116 which, in turn, connects to a branch connection at 117 with the duct 112 leading to cuff 101. Exhaust connections from deflate valves 103 and 104 are shown. Respectively, at 118 and 119. The valves 103 and 104 receive electrical control over a path 120 from the microprocessor 108.

The apparatus disclosed above with reference to FIG. 10. except for the plural deflate valves 103 and 104 and the programming of the microprocessor 108 herein, can be substantially the same as that disclosed in the patent application to M. Ramsey, III et al. which was first mentioned above. The structure disclosed in said application incorporates a single deflate valve while, as mentioned previously, the subject embodiment has two valves, 103 and 104, which valves preferably, but not necessarily, differ from one another with regard to orifice size. By way of example, valve 103 has a first size orifice and valve 104 has a larger size orifice, each valve being electrically actuatable and having a given finite response time under the control of microprocessor 108. The details of the microprocessor not discussed in said first mentioned patent application but necessary for the present invention will be apparent from the following discussion of the operation of the apparatus as disclosed herein.

Referring now to the operation of the apparatus illustrated in FIG. 10, it can be assumed that air under pressure of about 8-10 p.s.i. is available in the source of pressurized air 109. When it is desired to initiate a determination of blood pressure, the microprocessor 108 furnishes a signal over path 113 to open the inflate valve 111. It is assumed that the deflate valve apparatus 102 is closed. Air from the source 109 is communicated through valve 111 and duct 112 to inflate the cuff 101 to a desired level. Preferably, the microprocessor 108 responds to the signal from the pressure transducer 105. indicative of the instantaneous pressure in the cuff 101, to interrupt the inflation of the cuff 101 when the pressure in the cuff reaches a predetermined value above estimated systolic pressure. Such interruption will be accomplished by feeding a signal over path 113 to close inflate valve 111. Once valve 111 has been closed, the blood pressure measurement can be obtained by commencing the deflate routine.

Actual measurement of the blood pressure under the control of the microprocessor 108 and the deflate valve apparatus 102 and as sensed by pressure transducer 105 can be accomplished in any suitable manner such as that disclosed in said Ramsey, III patents or said above second mentioned Ramsey, III et al. patent application. At the completion of each measurement cycle, the deflate valve apparatus 102 can be re-opened as explained hereinafter long enough to relax the cuff pressure substantially completely. Thereafter, the deflate valve apparatus 102 can be closed at the start of a new measurement cycle.

By way of summation, when a blood pressure measurement is desired the inflate valve will be opened while the cuff pressure is supervised until the cuff pressure reaches the desired level at which time the inflate valve will be closed. Thereafter, the deflate valves are operated and the measurement taken. The operation of the apparatus that has been discussed to this point can be substantially the same as that described in the first mentioned patent application. The present invention relates to the deflation phase and that operation will now be described.

Typically, in prior art automatic sphygmomanometric devices, the cuff deflation operation has been accomplished in equal decremental steps, usually about 5 to 6 Torr, and invariably less than 7 Torr per step. However, it has now been discovered that reliable and accurate measurements can be obtained even though, contrary to long accepted precepts, steps substantially larger than 7 Torr are taken, and even though successive steps are of unequal magnitude. Consequently, in accordance with the present invention, the cuff deflation-measurement procedure is accelerated with a resultant significant reduction in overall cycle time. This is illustrated dramatically in FIG. 12 wherein the plot 130 shows that with equal size decrements on the order of 7 Torr per step, a complete cycle takes about 23 seconds. By contrast, the plot 131, representing operation of the apparatus embodying the present invention, shows completion of a full measuring cycle in less than 13 seconds. While the two plots 130 and 131 represent ideal cases wherein artifact has not interfered with and prolonged the measurement cycle, the plots do reveal the relative time acceleration that can be expected. The principles underlying the operation of the present invention are best described with reference to the flow chart in FIG. 11 to which attention should now be directed. At the commencement of the deflation operation or routine, the cuff is deflated by steps of predetermined fixed magnitude, generally between 5 and 7 Torr per step, until oscillations are detected and validated for the first time. The present example employs steps of 7 Torr each. Bearing in mind that the cuff pressure is at an upper level, the valve 103 with the smaller orifice is initially employed. For various reasons the subject apparatus is usually employed with the transducer 105 located up to 15 feet or more away from the cuff 101. This distance over which cuff pressure must be conducted via duct 106, as well as the inherent electromechanical limitations of the commonly used deflate valves, introduces a significant response time factor into the activation of the deflate valve apparatus 102. Therefore, the orifice of valve 103 must be small enough that the valve can be opened, cause a desired cuff pressure decrement, and be re-closed before a cuff pressure drop overshoot has occurred.

So long as the cuff pressure is relatively high the deflation velocity through the smaller orifice valve 103 will be high and the time required to decrement the pressure the desired step will be relatively short. This is reflected by the comparatively steep or substantially vertical step decrements 132 at the commencement of plots 130 and 131.

If the remaining deflation were to be accomplished only with valve 103 and with equal steps of 7 Torr each, the time for each decrement would increase, with each successive decrement, (because it occurs at a lower average pressure). and hence take longer and longer. This is represented by the "risers" 133 in plot 130 departing further and further from vertical as deflation progresses. The delay in the measurement is actually aggravated by the lengthened decrement interval because beyond a certain time interval the cuff will still be deflating when the next heart oscillation occurs and such oscillation will have to be skipped by the measuring apparatus, thus requiring a longer period of sampling at that cuff pressure.

The present invention avoids the above mentioned problem by timing each decrement step and by switching over to a larger deflate valve orifice whenever the decrement step requires more than 8 milliseconds to deflate 1 Torr. This is equivalent to a deflation rate of 125 Torr per second. Thus, during a deflation routine the present apparatus will at some point switch from deflate valve 103 to 104, and, if necessary, make a further switch to operation of both valves 103 and 104 in parallel. A typical deflation rate at the beginning of the deflation operation is about 200 Torr per second. This is equivalent to 5 mSec. per Torr.

As mentioned above and indicated by the flow chart in FIG. 2, after arterial oscillations are detected and verified i.e., oscillation amplitude is greater than 0, the microprocessor 108 resorts either to a look up table or to an equivalent formula to select a "Base" deflate step as a function of the then prevailing cuff pressure sensed by transducer 105. A typical table relating "Base" deflate step to cuff pressure can be constructed in the manner described below. Generally, the "Base" deflate steps over the middle range of the deflation procedure are each substantially greater than 7 Torr and can be as much as 20 Torr or more, particularly when measurements are being made on a subject with excessively high blood pressure.

The flow chart shows, however, an augmentation of the "Base" deflate step using the equation:

$$\text{Base} = \text{Base} + \text{PPA}/32 \quad (1)$$

wherein PPA is a quantity directly Proportional to the last detected oscillation peak amplitude. For convenience PPA can be replaced by "x", and for the purpose of generalization, the divisor "32", a constant unique to one specific embodiment, can be represented by the constant "a". The augmentation represented by equation (1) is used in the deflation routine until the microprocessor 108 has detected the maximum amplitude oscillation from the arterial complexes. After detection and verification of the maximum amplitude oscillation the decrement equation can be further augmented to:

$$\text{Base} = \text{Base} + \text{PPA}/32 + \text{PPA}/32 = \text{Base} + 2(\text{PPA}/32). \quad (2)$$

Operation in accordance with equations (1) and (2) therefore can be generalized as follows:

$$\text{Base} = \text{Base} + y(x/a) \quad (3)$$

where "Base" and "x" are as defined previously, "y" is equal to one or two, and "a" is a constant chosen such that the value of "x/a" over the normal range of oscillation amplitudes will vary between zero and about 3.

During each decrement step, a determination is made of the time required to accomplish the decrement and this time is stored to be used during the next decrement procedure. Also stored is the last "Base". By obtaining the quotient of the two stored quantities (Time/Base) and comparing with the preselected rate of 8 mSec.-/Torr. a determination is made whether to use the same (i.e. smaller) deflate valve for the decrement in process or to also use the larger orifice deflate valve in combination with the smaller valves. The drawings describe this particular scheme of operation for the valves.

The need for augmenting the cuff pressure dependent "Base" step by an oscillation amplitude dependent factor is due to two phenomena. First, there can occur a large increase in cuff pressure at each heart beat resulting from arm expansion momentarily during cardiac systole. Second, after the cuff pressure has decreased below that at maximum oscillation amplitude, the blood flow passing under the cuff 101 with each cardiac systole begins to engage the lower arm, which in turn, causes the pressure in the cuff to slowly rise. The net effect of the two phenomena is to require additional decrement steps in cuff pressure to deflate the cuff below the diastolic pressure level unless the deflate step sizes are increased commensurately with the two phenomena just described.

A look up table relating the "Base" deflate steps to prevailing cuff pressure can be constructed arbitrarily on a point by point basis or using the following type of equation:

$$\text{Base Step} = k(\text{CP}) \quad (4)$$

where "CP" = cuff pressure in Torr and "k" is a constant on the order of 0.1, for example.

Alternatively, when it is desired to place a constraint on the minimum size step, the equation can take the form:

$$\text{Base Step} = k_1 + k_2(\text{CP}) \quad (5)$$

Where "$k_1$" and "$k_2$" are constants. Respectively, on the order of 4 and 0.05, for example, and "CP" is as defined above.

It should be understood that equations such as (4) and (5) can be used directly to compute the values of Base Step as required during a measurement procedure instead of providing a pre-calculated look up table. It should also be understood that the value selected for "a" will depend upon the proportionality factor between "PPA" and actual oscillation peak amplitude.

Figure 11:
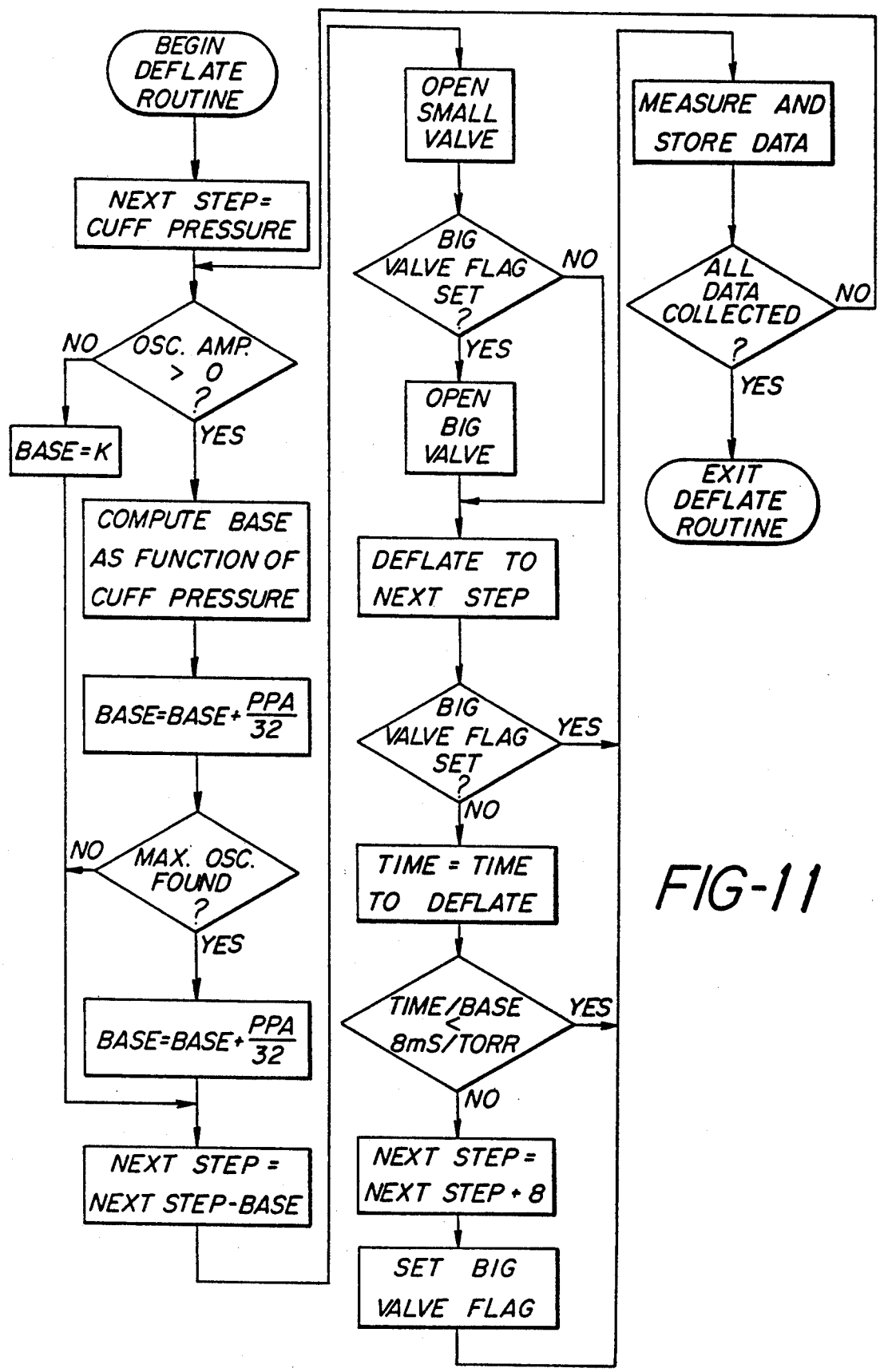
FIG. 11 is a flow chart representing the operation of the apparatus of FIG. 10 under the control of the microprocessor or equivalent controller.
Figure 12:
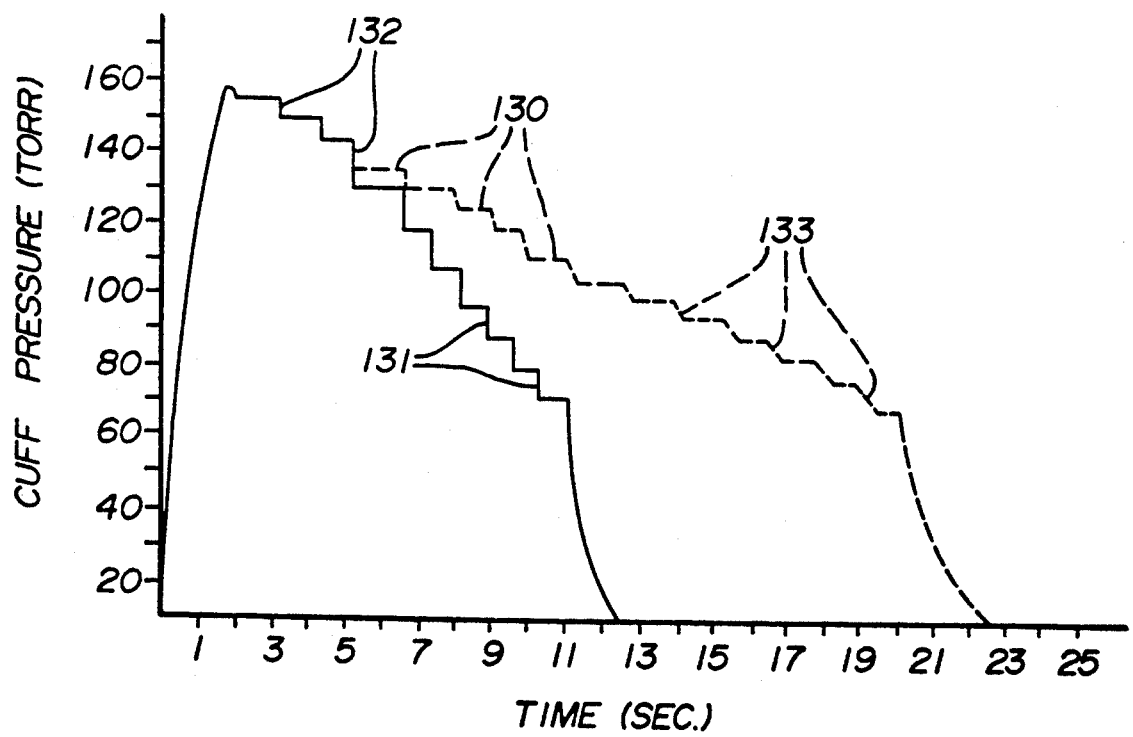
FIG. 12 is a pressure versus time graph comparing the operation of a prior art system with the operation of the present invention.

Referring to the flow chart of FIG. 11, it will be noted that when the 8 mSec./Torr decrement interval is exceeded, the NEXT STEP value (i.e., the desired new cuff pressure) is increased by "8". This is to ensure against overshooting the desired pressure level when first using the larger valve.

While valves 103 and 104 have been described as having different size orifices it is contemplated that equal size valves can be used. In such case, the operating routine would be arranged to commence the deflate cycle using one valve, with a switch to two valves in parallel when an increased flow rate for the particular pressure level is desired. Another alternative would be to have a controllable throttling valve operable between two or more orifice settings. In any event the deflate valve mechanism should have at least two operating modes, one providing a greater flow rate than the other for any given applied pressure.

The above-described arrangements are merely illustrative of the principles of the present invention. Numerous modifications and adaptations thereof will be readily apparent to those skilled in the art without departing from the spirit and scope of the present invention. For example, the pressure measurement mode is described above as stepped deflation from an initial inflation above the subject's systolic pressure. The measurement of the instant invention can alternatively be performed by stepped inflation from an initial sub-diastolic cuff pressure; or via continuous vis-a-vis discrete cuff inflation or deflation.

What is claimed is:

1. Apparatus for automatic measurement of systolic pressure of a subject comprising:
    a) an inflatable and deflatable pressure cuff;
    b) means for inflating said cuff to a predetermined pressure believed to be above systolic pressure;
    c) pressure transducer means for sensing cuff pressure including oscillation complexes therein;
    d) deflate means coupled to said cuff for controllably releasing pressure in said cuff;
    e) and processing means responsively coupled to said cuff pressure sensing means for providing blood pressure related measurements;
    f) means, responsive to the pressure signalled by said transducer, for generating a signal representative of oscillations complexes;
    g) complex peak storing means for storing values characterizing peak amplitudes of said complexes at different cuff pressures;
    h) cuff pressure storing means for storing cuff pressures respectively corresponding to said stored values;

and characterized by
- i) control means for causing said deflate means to employ deflation decrements at least during a substantial portion of the systolic measurement cycle, at a rate in excess of about 7 mmHg/sec.; and
- j) systolic pressure determining means including
  - i) means for locating the largest complex peak amplitude stored in said complex storing means and the cuff pressure corresponding thereto;
  - ii) means for generating a threshold level as a predetermined fraction of said maximum peak values;
  - iii) means for selecting plural peak amplitudes from those stored in said cuff pressure storing means, said plural peak amplitudes having predetermined relationship to said threshold and predetermined temporal relationship with the cuff pressure corresponding to said largest complex peak amplitude; and
  - iv) determining means for determining systolic pressure from said plural peak amplitudes.

2. Apparatus as described in claim 1 and further including data purifying means for correcting data inaccuracies among complex peak values stored in said complex peak storing means, and operative prior to said systolic pressure determining means.

3. Apparatus as described in claim 2 wherein a preselected character is stored in said complex peak storing means to signal an unsuccessful cuff pressure oscillation peak measurement, and wherein said data purifying means comprises means for examining the contents of said complex peak storing means and responsive to detecting said preselected character for replacing said character with a measure of plural stored complex peak values at least one of which was obtained at a cuff pressure lower than that associated with the preselected character.

4. Apparatus as described in claim 3 wherein said data purifying means includes means for searching said complex storing means for the occurrence of two equal peak amplitude values arising at successive cuff deflation pressures, and means responsive to said searching means for replacing one of the two stored equal values with a measure of two other values stored in said complex peak storing means.

5. Apparatus as described in claim 4 wherein said means for replacing includes means, responsive to said searching emans, for replacing one of the two stored equal values with the arithmetic average of two other values stored in said complex peak storing means.

6. In an automatic oscillometric blood pressure monitor employing a pressurized cuff, means for deflating said cuff, and means for measuring arterial pressure oscillation complexes and the peak of the envelope thereof through measurement of prevailing and time varying cuff pressures, a method for measuring systolic pressure comprising the steps of
- a) deflating said cuff, at least during the systolic portion of the blood pressure measurement cycle, in decrements at a rate in excess of about 7 mmHg/sec.;
- b) at each said decrement level, detecting oscillation complexes, measuring and storing the peak of the envelope thereof, and storing identification of the associated prevailing decrement level;
- c) examining the sequence of said peaks relative to a predetermined overall sequence, and substituting an appropriate value for each associated value which departs in predetermined fashion from said sequence;
- d) finding the amplitude $\Phi A(MAX)$ of the largest of said peaks;
- e) developing an amplitude reference LVL which is a predetermined fraction of $\Phi A(MAX)$;
- f) identifying a pair of decrement levels L and L+1 which are prior in time to the level at which $\Phi A(MAX)$ occurred, and which respectively precede and follow a cuff pressure associated with said amplitude reference LVL; and
- g) developing systolic pressure as the interpolated cuff pressure between said pressure levels at L and L+1, assuming a predetermined functional progression in amplitude between $\Phi A(L)$ and $\Phi A(L+1)$.

7. A method as described in claim 6 wherein said predetermined functional progression is a linear function of time.

* * * * *